United States Patent [19]
Wittler

[11] Patent Number: 4,997,660
[45] Date of Patent: Mar. 5, 1991

[54] METHOD AND APPARATUS FOR CONTROLLING FOAM IN A VINEGAR FERMENTATION PROCESS

[75] Inventor: Rüdiger Wittler, Siegburg, Fed. Rep. of Germany

[73] Assignee: Heinrich-Frings GmbH & Co. KG, Bonn, Fed. Rep. of Germany

[21] Appl. No.: 447,993

[22] Filed: Dec. 8, 1989

[30] Foreign Application Priority Data

Dec. 13, 1988 [AT] Austria .................................. 3034/88

[51] Int. Cl.$^5$ .......................... B01D 19/00; C12J 1/00
[52] U.S. Cl. ......................................... 426/17; 55/178; 99/323.12; 426/478; 435/812
[58] Field of Search ........................ 435/140, 246, 812; 426/17, 478; 202/264; 203/20; 261/DIG. 26; 55/178; 99/323.12

[56] References Cited

U.S. PATENT DOCUMENTS

| | | | |
|---|---|---|---|
| 3,262,252 | 7/1966 | Ebner ..................... | 55/178 |
| 3,693,325 | 9/1972 | Muller ................... | 435/812 |
| 3,813,086 | 5/1974 | Ebner et al. ........... | 261/93 |
| 4,340,677 | 7/1982 | Hitzman ................ | 435/246 |
| 4,373,024 | 2/1983 | Hunt ..................... | 435/812 |

FOREIGN PATENT DOCUMENTS 206866 12/1959 Austria .
505637 4/1971 Switzerland .

Primary Examiner—George Yeung
Attorney, Agent, or Firm—Norbert P. Holler

[57] ABSTRACT

A method and apparatus for controlling the foam in a vinegar fermentation process. As in the prior art, the foam accumulating on the upper surface of the fermentation substrate is moved along a given path axially through a rotor of the apparatus and revolved about the path by the rotor so as to be subjected to centrifugal forces and broken up into a gas portion which is exhausted in the direction of movement along the path and a liquid portion, possibly still including some foam particles, which is separated from the gas portion in a direction radially of the path. According to the invention, in order to minimize the foam accumulation in the fermentation tank, it is proposed to completely eliminante the liquid portion of the broken-up foam from the fermentation process, i.e., not to recycle the separated liquid portion into the fermentation tank, either by disposing of it or by further processing it and/or mixing it with the recovered vinegar end product apart from the fermentation process.

18 Claims, 4 Drawing Sheets

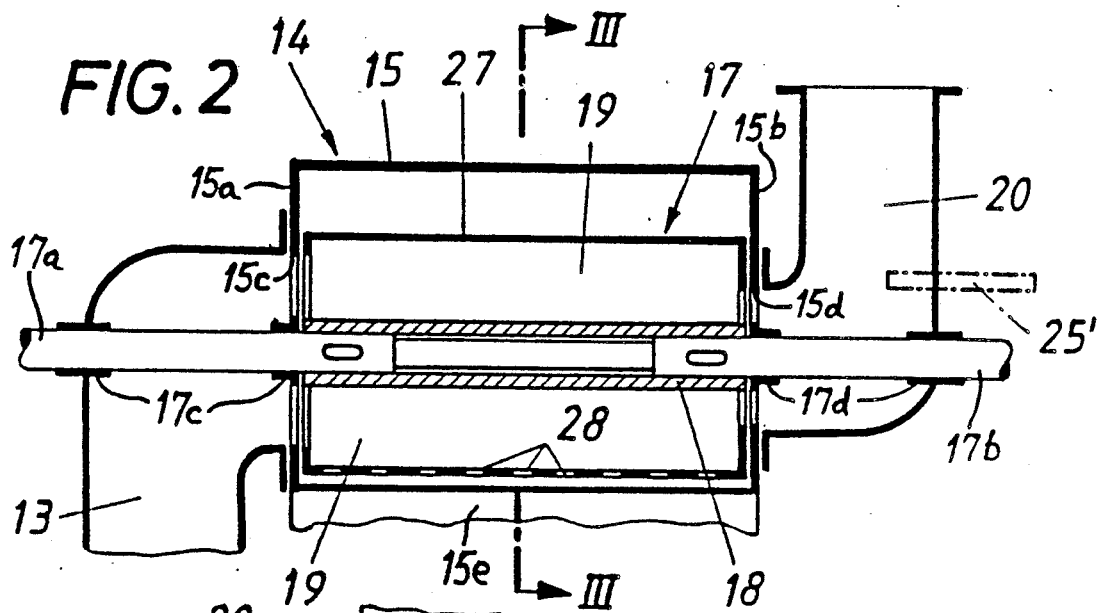
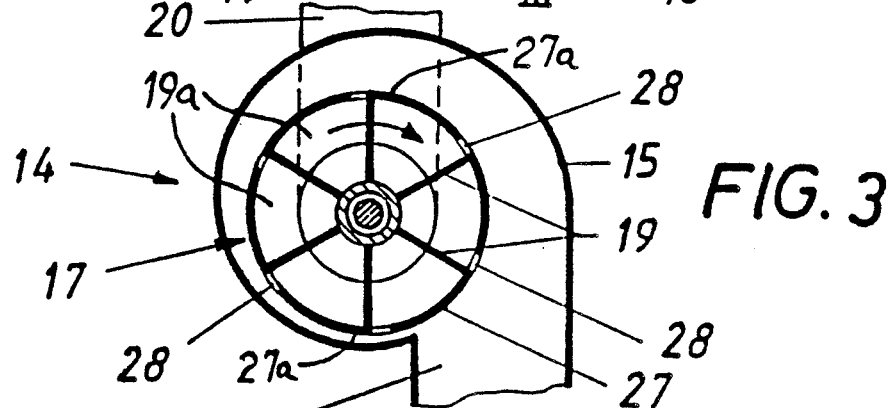
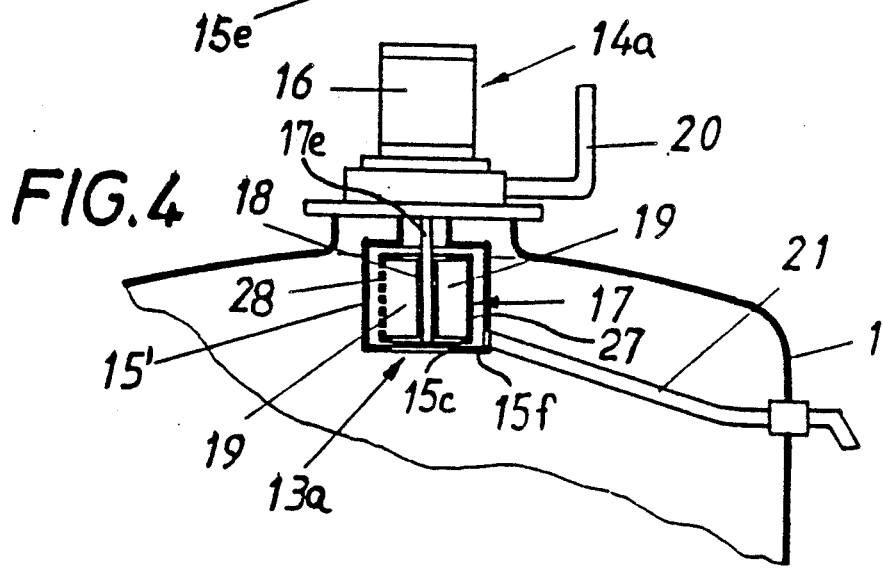

METHOD AND APPARATUS FOR CONTROLLING FOAM IN A VINEGAR FERMENTATION PROCESS

This invention relates to a method and apparatus for controlling foam in a vinegar fermentation process.

BACKGROUND OF THE INVENTION

In vinegar production, there have heretofore been two possible ways of dealing with the accumulation of foam during the fermentation process. One way entails the use of a mechanical defoamer or foam breaker, with the separated liquid portion of the foam being recirculated back into the fermentation tank, while in the other way it is necessary to permit the accumulating foam to overflow into a seperate collecting vessel. In either case, however, the foam, after being clarified and filtered, ultimately has to be reused in the fermentation process, because the quantity of foam that is generated is simply too large to be disposed of. In the production of high percentage alcohol vinegar, the foam formation is in the first instance dependent on the operational qualities of the fermenter. If the fermenter runs so well that a substantial harming of the vinegar bacteria is avoided, relatively little foam will be generated. If the fermenter operation, on the other hand, is mildly defective, which will be the case with most fermenters and may, for example, be due to a less than ideal aeration or cooling of the fermenting liquid or a deficiency in the injection of mash into the fermenter, the resultant appreciable harming of the vinegar bacteria will lead to a substantial generation of foam. This in and of itself might still be tolerable and permit the fermenter to be run without the aid of a defoamer.

One can never fully exclude the possibility, however, that a complete breakdown of the fermentation could occur, caused, for example, by a relatively brief power outage or by a running of the fermentation at a zero percent alcohol concentration in the event of a malfunction of the alcohol feed system. Should that happen, almost all the vinegar bacterial will die suddenly and an extraordinarily high degree of foaming will result, with liquid constituting up to 50% of the foam and it being impossible to discern the boundary between liquid and foam in the fermenter. If this foam were to be vented to the outside of the fermenter in the absence of a mechanical defoamer, the entire contents of the fermenter would be transformed into foam and emptied out of the same in a relatively brief time interval. Thus, the use of a mechanical defoamer or foam breaker is absolutely essential in such a case, in order to control the high foam pressure created in the fermenter and to minimize the formation of foam.

It might be noted, in passing, that in the production of malt vinegar, wine vinegar and fruit vinegar, the use of a mechanical defoamer is always required, because such mashes inherently tend to foam since they are infected with bacteria which die in the fermenter.

In order to avoid the necessity of having to break up the foam accumulating in a fermentation tank during a vinegar fermentation process completely into a gaseous and a liquid portion, it is known from Austrian Patent No. 206,866 and its corresponding U.S. Pat. No. 3,262,252, the disclosure of which is incorporated herein by this reference, to withdraw the foam from the fermenter into an apparatus which includes a generally cylindrical housing arranged to be traversed axially by the foam, and a motor-driven rotatable member or rotor disposed in the housing and journaled for rotation about an axis parallel to or coincident with the axis of the housing, the rotatable member comprising a hub or axle carrying a plurality of radial vanes defining therebetween a plurality of circumferentially adjacent, axially extending, cross-sectionally generally V-shaped, open-topped passageways. Thus, as the foam moves axially through the housing, it is subjected, when contacted by the vanes of the rotating member, to centrifugal forces, which leads to a radially outward displacement of the liquid portion of the foam and a separation thereof from the main gaseous portion and permits the gas to be axially withdrawn from the rotating member and the housing both liquid-free and foam-free. The liquid portion, which is so denoted even though it may still have some foam remnants (herein referred to as foam particles) attached to it, is removed through a liquid discharge outlet in the housing wall and is recycled into the fermentation tank for remixing with the fermentation substrate, in connection with which an unobstructed circuit for foam movement between the fermenter and the rotatable member is established in order to obviate having to undertake a complete, high energy-consuming, break-up of the foam into separate gaseous and liquid portions.

This circulation of the liquid portion of the foam back to the fermenter has proved to be satisfactory in regularly conducted fermentation processes but, when something interferes with the smooth running of the process, can lead to an excessive foam buildup, so that the drive motor for the rotating member becomes overloaded and the foam break-up is interrupted, which in turn can ultimately lead to an interruption of the entire fermentation process. Such an excessive foam build-up can, by way of example, occur during a submerged vinegar fermentation if the vinegar bacteria are damaged by virtue of an insufficiency in the oxygen supply, a too rapid change in either the alcohol concentration or the acetic acid concentration, or an operator's error.

BRIEF DESCRIPTION OF THE INVENTION

The objective of the present invention is to avoid the aforesaid drawbacks and disadvantages and to provide an improved method and apparatus for controlling the foam in a submerged vinegar fermentation process, which method and apparatus make it possible that the foam load can be substantially reduced without it being necessary to increase the energy required for the separation of the foam into gas and liquid fractions.

The invention achieves this objective by virtue of the fact that, contrary to what is done in the above-described known process, the liquid portion of the foam (possible, as previously mentioned, still carrying some foam remnants) which accumulates during the break-up of the foam is not recirculated to, and thus is eliminated from, the fermentation process.

By dispensing with a circulation of the liquid portion of the extracted foam back into the fermenter and utilizing instead thereof a removal of the liquid portion entirely from the fermentation process, the tendency for the foam to build up in the fermentation tank is surprisingly substantially reduced, apparently for the reason that the surface-active substances which result from a partial lysis of damaged bacteria and which constitute the principal source for the foam build-up, and which are extracted from the fermenter together with the foam, no longer reenter the fermentation substrate through the intermediary of the separated liquid portion and hence cannot initiate a fresh foam build-up in the fermenter. This results in a less turbulent fermentation process with a substantially reduced foam build-up, by virtue of which the overall fermentation process loses only an amount of liquid which is negligibly small relative to the volume of the fermentation substrate.

Since the elimination of the liquid portion of the foam from the fermentation process as a concomitant of the foam break-up tends to inhibit an increase in (i.e., an amplification of) the foam build-up which otherwise would occur by virtue of the recirculation of the foam-generating substances into the fermentation substrate, the foam build-up remains, even in the event of an operating breakdown, within generally tolerable limits. Over and above that, the reduced foam build-up leads to a lower energy requirement for the break-up of the foam, so that overall a higher operating efficiency can be achieved.

The liquid portion of the foam separated from the fermentation process can either be disposed of or further processed, e.g., by means of a special filtration, independently of the vinegar end product extracted from the fermentation process. With respect to such further processing, of course, a special capability exists by virtue of the present invention, namely, that the liquid foam portion separated from the fermentation process can be mixed with the extracted vinegar end product outside the fermenter. To this end, the liquid foam portion recovered from the at least temporarily continuing foam build-up is preferably collected and stored prior to any further processing thereof, which above all is highly recommended in the case of an intermittent accumulation of the end product.

For the performance of the process of the present invention, the starting point may be an apparatus of the general type disclosed in the abovementioned U.S. Pat. No. 3,262,252 and Austrian Patent No. 206,866. Such an apparatus thus would include a rotatable member or rotor journaled in a generally cylindrical housing, which member has a hub carrying a plurality of radial vanes and provides a plurality of axial recesses defined between the vanes. The apparatus would further be provided at one end face of the housing with a foam inlet opening connected to the fermenter, at the other end face of the housing with a gas exhaust opening, and in one region of the housing intermediate the opposite ends thereof with a liquid discharge opening. For the purposes of the present invention, in such an apparatus the discharge opening may then be connected with a drainage duct leading to a suitable location outside of the fermenter. On the other hand, in the event the liquid foam portion eliminated from the fermenter is not to be disposed of but rather is to be further processed, then the discharge opening can be connected via the drainage duct with a collecting vessel separate from the fermenter, in order to enable the liquid portion of the foam (which may, as mentioned, still have foam particles attached thereto) to be temporarily stored before being further processed alone or being admixed, for joint further processing, with the vinegar end product extracted from the fermenter.

The relatively limited quantity of foam that accumulates in the fermenter due to the practice of the present invention makes it possible to enhance the breaking of the foam into gas and liquid fractions without having to increase the requisite energy consumption for this purpose. To this end, the rotatable member may further include a surrounding cylinder or sleeve jointly rotatable therewith, which sleeve or cylinder is supported on the hub by means of the radial vanes (i.e., is attached to the vanes at their radially outwardmost end edges) and is provided in its wall with radial through openings located close to the vanes and trailing the same as viewed in the direction of rotation of the rotor. By virtue of this construction, the foam entering into the axially extending chambers of the rotatable member within the confines of the surrounding cylinder is, after its being engaged by the vanes, not centrifuged directly into the housing surrounding the rotating member but rather is compressed against the inner wall surface of the rotating cylinder and in particular first in the imperforate regions of the wall sections of the cylinder which are proximate to and ahead of (i.e., in leading relationship to) the respective vanes as viewed in the direction of rotation. Thus, the liquid foam portion accumulating in each space defined between two successive vanes must first spread out from the trailing one of the two vanes in the direction of rotation of the rotatable member along the respective section of the inner wall surface of the rotating cylinder up to the leading one of the two vanes before it can pass out of the cylinder and into the housing through the radial openings in the cylinder. The associated enhanced centrifugal force action thus aids the expulsion of the gas portion of the foam axially out of the rotatable member and thereby makes certain the sought-for improvement of the break-up of the foam into gas and liquid portions.

The reduction in the build-up of foam which is achieved by the method according to the present invention entails the advantage that it leads directly to a reduction in the size of the apparatus for breaking the foam up into gas and liquid portions. This makes it possible, especially in the case of smaller fermenters, to arrange the rotatable member not for rotation about a horizontal axis but rather for rotation about a vertical axis, with the foam inlet to the apparatus in the latter case consisting of an axial lower opening of the housing on the end section of the same which extends down into the fermenter, so that especially advantageous constructional conditions can be maintained which enable further simplifications to be achieved (e.g., the elimination of one of the bearings of the axle for the rotatable member) when the rotatable member is arranged in an endwise suspended position.

In accordance with another variant of the invention, the foam break-up apparatus need not be provided with a housing surrounding the vertically oriented rotatable member but instead can include, for facilitating the removal of the separated liquid portion, a rotatable member in which the cylinder or sleeve that is supported on the hub by means of the radial vanes has at least one end region projecting axially beyond the vanes, with the liquid drainage duct which extends to the outside of the fermenter being disposed in communication, by means of an intake opening oriented counter to the direction of rotation of the rotatable member, with the interior of that section of the cylinder which extends beyond the vanes. Through this construction, the liquid which accumulates against and rotates with the inner wall of the cylinder section that projects axially beyond the ends of the radial vanes is pressed into the drain conduit and is forced through the same out of the fermenter, all of which can be achieved with the aid of relatively minimal construction costs. Since the rotatable member in this variant is journaled for rotation about a vertical axis, the lower end section of the cylinder that extends downwardly beyond the vanes simultaneously defines the foam inlet of the apparatus. The rotational energy of the liquid in the region of the projecting section of the cylinder is then so great that a pressure feeding of the separated liquid even through a drainage duct directed upwardly out of the fermenter becomes possible.

The vertically disposed rotatable member, of course, needs to be driven only in case of an accumulation of a predetermined amount of foam. It is advantageous, therefore, to provide means for inhibiting a reverse flow of the separated liquid portion back into the fermenter from the drainage duct and the rotatable member whenever the rotation of the latter is interrupted. In accordance with another variant of the invention, such a reverse flow of the separated liquid back into the fermenter can advantageously be inhibited by providing a collecting channel at the lower end of the downwardly projecting section of the rotatable cylinder and disposing the intake end of the vertically upward running drainage duct so as to extend into the channel with the intake opening of the duct facing counter to the direction of rotation of the rotatable member. The same back flow prevention can, however, also be achieved by providing both the collecting channel and the intake opening of the drainage duct at the same end of the vertical cylinder of the rotatable member as where the gas exhaust opening of the latter is located, i.e., at the upper end of the cylinder.

BRIEF DESCRIPTION OF THE DRAWINGS

The foregoing and other objects, characteristics and advantages of the present invention will be more clearly understood from the following detailed description thereof when read in conjunction with the accompanying drawings, in which:

FIG. 2 is an axial section, on a greatly enlarged scale, through the foam break-up apparatus provided in the foam control system of FIG. 1;

FIG. 3 is a sectional view taken along the line III—III in FIG. 2;

FIG. 4 is a fragmentary schematic vertical section through a fermenter equipped with a modified form of the apparatus for breaking the accumulating foam into gas and liquid portions, the apparatus here having a rotatable member arranged for rotation about a vertical axis;

DETAILED DESCRIPTION OF THE INVENTION

Figure 1:
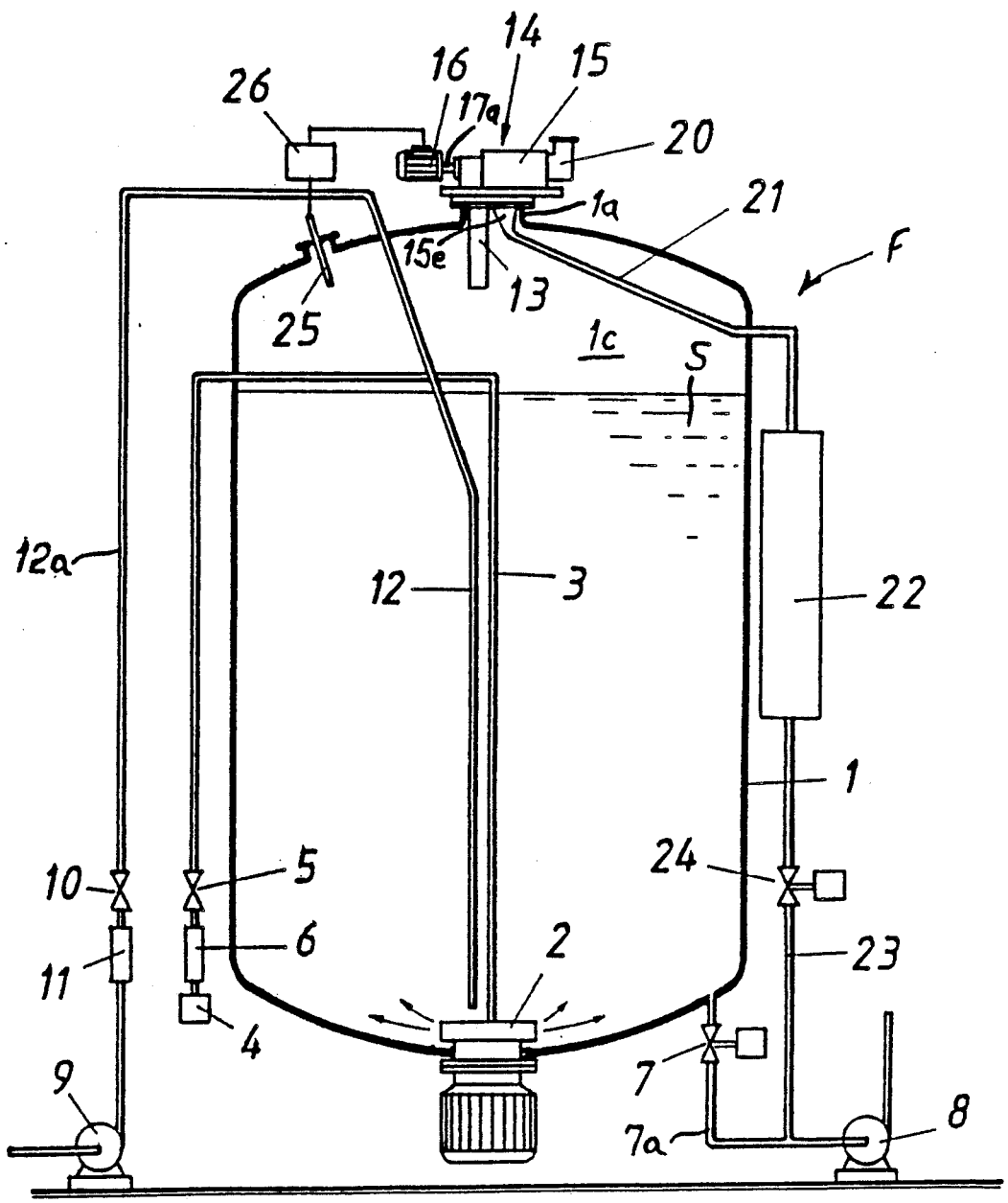
FIG. 1 is a schematic vertical section through a fermenter designed for the performance of a submerged vinegar fermentation and including a foam control system provided with a foam break-up apparatus according to one embodiment of the present invention.

Referring now to the drawings in greater detail, FIG. 1 shows a fermenter F which is designed for performing submerged vinegar fermentations and in conventional manner includes a fermentation tank 1 provided at the bottom with a motor-driven aeration device 2, for example, an aerator such as is disclosed in U.S. Pat. No. 3,813,086. The aerator is connected with an air aspiration pipe 3 through which the quantity of air required to provide oxygen for the vinegar bacteria is aspirated from outside the tank via a filter 4, a metering valve 5 and a flow meter 6. A suitable, for example, solenoid-operated, control valve 7 and a delivery pump 8 are incorporated in a discharge duct 7a connected at one end to the bottom of the fermentation tank and leading to a receiving vessel (not shown), in order to enable a predetermined quantity of the vinegar end product of the fermentation process to be extracted from the tank at the end of a specified fermentation period, for example, when a predetermined residual alcohol content of the fermentation substrate S has been attained in the fermenter. To enable an extracted quantity of the vinegar end product to be replaced by a quantity of fresh mash, the fermenter is provided with a feed pipe 12 located within and substantially axially of the tank and having its discharge end located in close proximity to the rotor (not shown) of the aeration device 2, the section 12a of the pipe exteriorly of the tank being connected with a mash reservoir (not shown) and having incorporated therein a feed pump 9, a metering valve 10 and a flow meter 11. This arrangement, which per se is well known, is designed to ensure a uniform and thorough mixing of the injected mash with the fermentation substrate S under simultaneous aeration.

The tank 1 at its top has an opening 1a sealed by a cover plate 1b on which is mounted an apparatus 14 according to one embodiment of the present invention for the dual purpose of extracting from the fermenter the foam which forms in the course of a submerged vinegar fermentation and accumulates in the tank space 1c above the top surface of the fermentation substrate, and of breaking up the accumulating foam into a gas portion and a liquid portion, the latter of which may have some residual foam particles adhering thereto. The apparatus 14 includes a horizontally oriented, cross-sectionally generally cylindrical housing 15 (see also FIGS. 2 and 3) which has end walls 15a and 15b provided with respective openings 15c and 15d. Of these, the opening 15c, which is larger than the opening 15d, is in communication with one end of a foam intake duct 13 that extends through the tank cover 1b into the tank 1, while the smaller opening 15d is in communication with one end of a gas vent or exhaust duct 20. The housing 15 at one side thereof has a generally tangential liquid discharge opening or outlet 15e which is in communication with a generally downwardly extending drainage duct 21. Rotatably mounted in the housing 15, through the intermediary of horizontal shaft members 17a and 17b journaled in respective bearings 17c and 17d, is a rotatable member or rotor 17 basically constructed of a hub or axle member 18 which is keyed to the shaft members 17a, 17b and carries a plurality of circumferentially spaced radial vanes 19 extending the full length of the hub. The vanes thus define therebetween a series of axially extending, generally V-shaped and radially outwardly flaring, passageways 19a into and through which foam withdrawn from the tank 1 via the duct 13 can pass. The shaft member 17a is connected with a drive motor 16 arranged to be activated and deactivated by a suitable control device 26 responsive to a foam level-sensing device 25 extending into the tank. The sensing device 25, details of which are not shown but which is well known per se, in conventional fashion includes two spaced electrodes electrically insulated from each other and connected with the energization circuit for the control device 26. The arrangement is such that when foam enters the space between and contacts the two electrodes, the said energization circuit is closed and the motor 16 set into operation to drive the rotor 17.

It will be apparent, therefore, that in operation of the apparatus 14 as so far described (in which the rotor 17 has essentially the same form as the rotor of the foam break-up apparatus described in U.S. Pat. No. 3,262,252 and Austrian Patent No. 206,866), any foam entering the housing 15 and moving along the path extending between the openings 15c and 15d and through the passageways 19a is engaged by the vanes 19. It will be understood, in this regard, that when foam in the fermenter space 1c builds up to the foam entry opening of the apparatus 14, there is immediately created, by virtue of the smaller area of the gas exhaust opening 15d relative to the foam entry opening 15c, an overpressure in the fermenter which forces the foam into the apparatus 14. Thus, when the rotor 17 is in rotation, the centrifugal forces exerted on the foam flowing axially through the passageways 19a cause a breaking up of the foam, i.e., a separation of the liquid portion of the foam from the gas portion thereof. This is due to the fact that the gas portion, by virtue of its lighter mass, remains closer to the hub of the rotor 17 and is removed axially from the housing through the exhaust opening 15d and the 15d and the exhaust duct 20, whereas the heavier, possibly still foam-loaded, liquid portion is centrifuged radially out of the open-topped passageways 19a of the rotor 17 into the housing 15 and is removed therefrom through the discharge opening 15e and the drainage duct 21. The liquid fraction then can be either disposed of (not shown) or alternatively can be led via the duct 21 into a collecting vessel 22 for storage preparatory to being subjected to a further processing.

By means of this manner of total elimination of the liquid portion of the accumulating foam from the fermentation process, i.e., without any recirculation of the liquid back into the fermentation tank, a further foam build-up that could be caused by the surface-active substances found in this liquid portion (such surface-active substances result from a partial lysis of harmed vinegar bacteria and actually cause the foaming) is avoided. As a consequence, the vinegar fermentation is rendered less turbulent and a substantially minimized foam formation can be expected. Such a minimized foam formation also permits the liquid portion accumulating during the break-up of the foam to be separated from the fermentation process without causing any problems in the latter due to loss of liquid, because the removed liquid portion has a negligibly small volume relative to the contents of the fermenter.

As previously indicated, the liquid portion of the foam accumulating and stored in the collecting vessel 22 can be extracted from the vessel as needed, and in particular this can be done advantageously at the time of an extraction of vinegar end product from the fermenter, in order to enable the accumulated liquid portion to be mixed and further processed with the extracted vinegar. For this purpose, the collecting vessel 22 is connected to the intake side of the delivery pump 8 by means of a discharge conduit 23 and through a suitable control valve 24, while at the same time the control valve 7 is open as well. The vessel can, however, also be connected via the control valve 24 and the feed pump 8 directly to a further processing location, for example, a filtration system, without being mixed with the vinegar end product, and at such time the valve 7 would, of course, be closed.

By virtue of the minimal foam formation achieved by the method of the present invention, the apparatus 14 is designed to be activated only upon a predetermined foam build-up in the tank 1. To this end, the foam sensor 25 serves to detect the height of the accumulated foam in the fermenter and to energize the motor 16 through the control device 26 in dependence on the detected foam height. In order, however, in accordance with a refinement of the present invention, to prevent an undesired power-consuming and energy-wasting energization of the motor 16 by foam particles becoming or remaining stuck between the electrodes of the foam sensing device even though the foam level may be or have sunk below that of the sensor electrodes 25, the latter can also be arranged in the gas exhaust duct 20, i.e., beyond the location of the gas exhaust opening 15d, as is indicated in dot-dash lines at 25' in FIG. 2. With such an arrangement, it will be understood, the sensor electrodes will be contacted by foam and the motor will be started only when and as soon as some of the foam has been forced through and out of the rotor 17 via the gas exhaust opening 15d by the overpressure existing in the fermentation tank. Once the rotor starts rotating, of course, further passage of foam through the opening 15d stops immediately. Since that would also stop the motor (the flow of gas out of the rotor would have blown any foam particles off the sensor electrodes 25'), a time delay holding relay (not shown) is provided to maintain the motor energization circuit closed for a predetermined time interval sufficient to reduce the built-up foam in the fermenter to a desired level. After the relay has stopped the motor, the cycle is repeated, with foam building up and some of it eventually contacting the sensor electrodes 25' to again start the motor and lock in the holding relay until the preset time interval of operation of the apparatus 14 has expired.

The minimal foam build-up achieved by the present invention further makes it possible to achieve an even better break-up of the foam. For this purpose the rotor 17 is provided with a jointly rotatable cylinder or sleeve 27 affixed to and supported by the vanes 19 at their radially outwardmost extremities, so that the axial foam passageways 19a defined between the radial vanes 19 are closed at their radially outer peripheries by the respective segmental sections of the cylindrical sleeve 27. In conjunction therewith, the sleeve 27 is provided with a plurality of through openings 28 for permitting escape of the liquid portion of the foam into the housing 15, the openings being arranged in sections of the sleeve wall which are adjacent the vanes 19 but trail the same as viewed in the direction of rotation of the rotatable member 17 (see FIG. 3). The arrangement is such that the liquid foam portion which is centrifugally displaced radially outwardly of the rotor in the passageways 19a first accumulates at and is compressed against the imperforate regions of the wall sections of the sleeve or cylinder 27, i.e., at the regions 27a of those wall sections which are adjacent to but are ahead of or lead the respective vanes as viewed in the direction of rotation, and only then spreads or expands over the remainders of the wall sections up to the locations of the respective through openings 28 adjacent the next successive vanes 19, to enable the liquid portion of the foam to be slung or centrifuged outwardly through the openings 28 into the housing 15. In this way, a somewhat larger quantity of gas than would otherwise be the case is separated from the liquid portion of the foam, which has the advantageous effect of minimizing the required take-up volume of the collecting vessel 22.

In the embodiment of the invention illustrated in FIGS. 1-3, the apparatus 14 for breaking up the accumulating foam into liquid and gas portions is conventionally arranged with its axis of rotation oriented horizontally on the fermentation tank 1. However, the reduced energy consumption for the foam break-up made possible by the minimized foam build-up in the fermenter through the method of the present invention further provides the capability, especially in the case of smaller fermenters, of arranging on the tank 1 an apparatus 14a (see FIG. 4) which is provided with a rotor 17 mounted for rotation about a vertical axis of rotation. In this embodiment of the invention, the associated housing 15', which surrounds the rotor 17 and in which an axial end opening 15c, as before, defines the foam inlet 13a of the apparatus, extends endwise down into the fermenter, with the shaft 17e which carries the hub 18 of the rotatable member 17 advantageously being supported at one end only (the upper end) and enabling the attainment of a foam intake unobstructed by a bearing for the shaft. All other parts of the apparatus 14a are essentially the same as in the embodiment of FIGS. 1-3, except that no special foam intake duct 13 is required and that the generally downwardly slanted drainage duct 21 extends through the tank 1 and communicates with the housing 15' adjacent the free end thereof where the cylindrical wall of the housing adjoins a radial end flange 15f thereof which defines the end face of the housing and the opening 15c therein.

The apparatus according to the present invention for breaking up the foam in the fermenter into liquid and gas portions can also be constructed to have a rotor mounted for rotation about a vertical axis but without being enclosed in a surrounding stationary housing. This variant construction can be incorporated in embodiments of the invention represented by FIGS. 5, 6 and 7.

Figure 5:
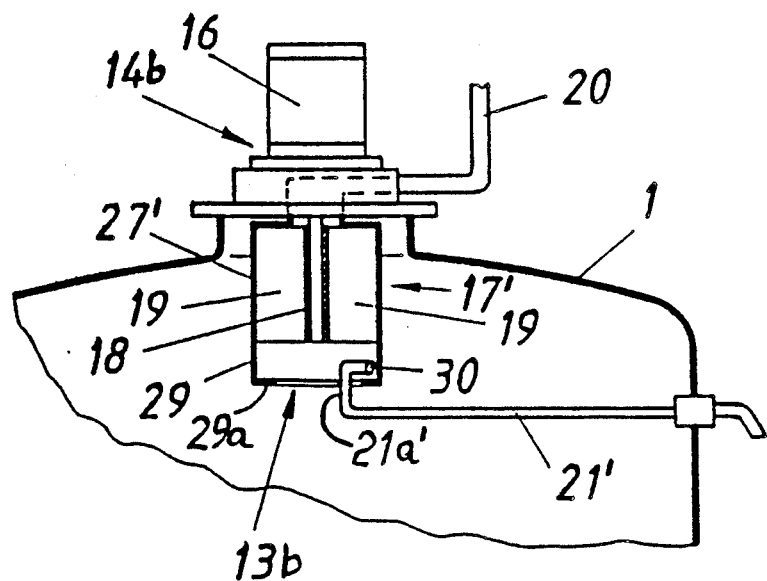
FIG. 5 is a view similar to FIG. 4 and shows a further modified foam-breaking apparatus which has a vertically rotatable member and a horizontal drainage duct for extracting the liquid portion of the broken-up foam directly from a collecting section of the associated rotatable cylinder.
Figure 6:
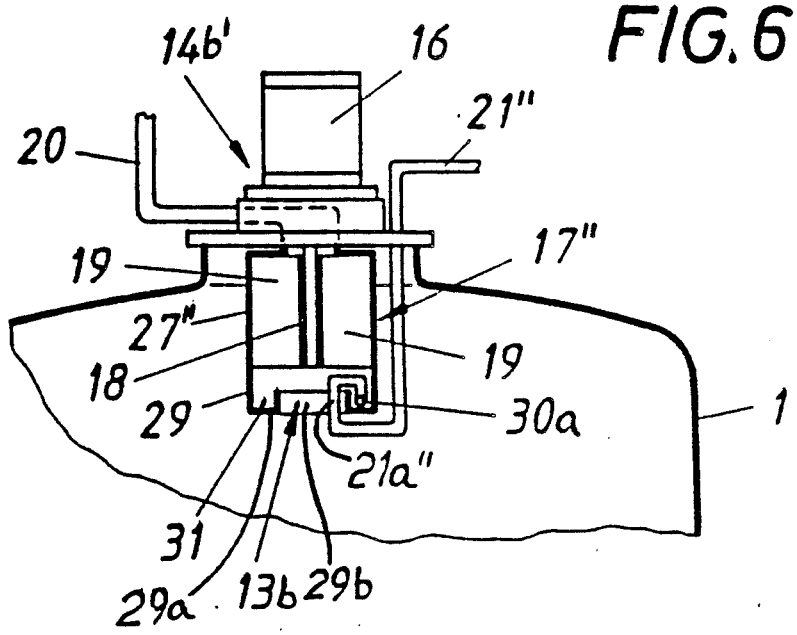
FIG. 6 is a view similar to FIG. 5 and shows a still further modified version of the apparatus and a vertically upwardly extending drainage duct for extracting the liquid portion of the foam upwardly from the rotatable cylinder.

More particularly, in each of the embodiments of FIGS. 5 and 6 the respective apparatus 14b or 14b' includes a vaned rotatable member, designated 17' in FIG. 5 and 17" in FIG. 6, the cylindrical sleeve 27' or 27" of which is imperforate throughout. In each case, however, the sleeve extends downwardly into the fermenter beyond the lower ends of the respective radial vanes 19 and thereby provides a projecting cylindrical section 29 at the lower end of which the foam inlet 13b is defined by a radially inwardly directed annular end flange 29a. In the embodiment of FIG. 5, the liquid foam portion separated by centrifugal force from the gas portion during the rotation of the rotor 17' accumulates in the section 29 interiorly of the cylinder and above the annular end flange. To enable this liquid portion of the foam to be extracted directly from the interior of the sleeve section 29, the drainage duct 21', which is shown as oriented horizontally but may be downwardly inclined, is provided with an intake end section 21a' which extends into the sleeve section 29 and there has an inlet opening 30 positioned close to the inner wall surface of the sleeve section 29 just above the end flange 29a and oriented counter to the direction of rotation of the rotatable member 17'. Thus, the liquid accumulating in the cylinder 27' and rotating therewith is forced into the drainage duct 21'.

The same principle makes it possible, in the embodiment of FIG. 6, to provide an apparatus 14b' which includes a drainage duct 21" that extends vertically upwardly out of the fermenter through the tank cover supporting the apparatus 14b'. However, in this embodiment measures must be taken to inhibit any reverse flow of the liquid in the discharge conduit 21" back into the fermenter 1 when the rotation of the rotatable member 17" is interrupted. To this end, the downwardly projecting section 29 of the cylinder or sleeve 27" is further provided with an axial annular flange 29b at the inner periphery of the radial end flange 29a so as to define an upwardly open collecting channel 31 at the free end of the cylinder section 29. The intake end section 21a" of the drainage duct 21" here projects into the channel 31 and has its inlet opening 30a positioned close to the bottom of the channel and, as before, oriented counter to the direction of rotation of the rotatable member 17". The volume of the channel 31 must, of course, be sufficient to enable the channel to catch and retain all of the separated liquid that is present in and flows back downwardly out of the vertically rising drainage duct when the rotation of the rotor is interrupted.

Figure 7:
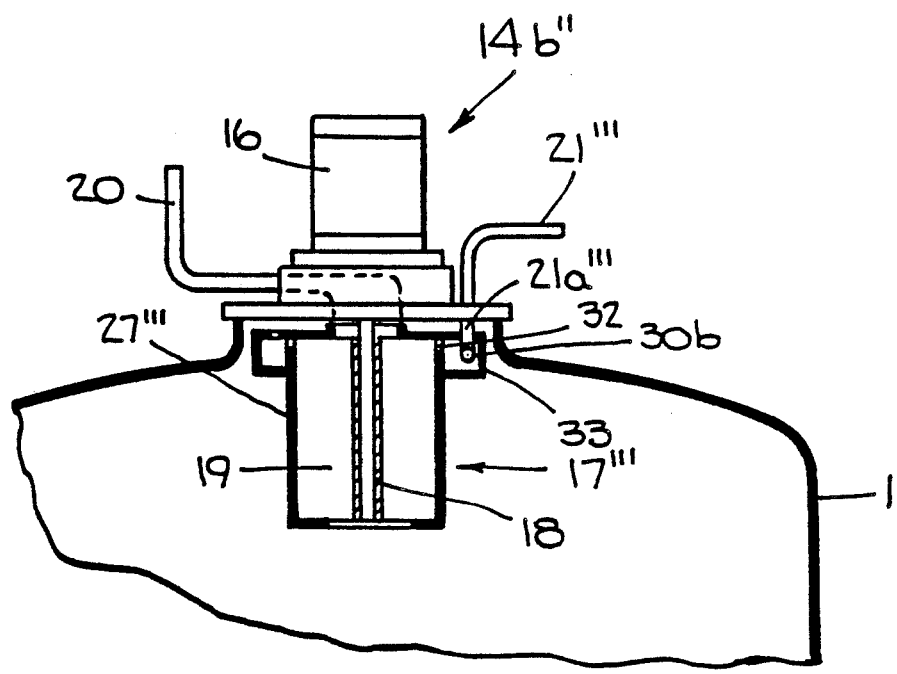
FIG. 7 is a view similar to FIG. 6 and shows yet another modified form of the apparatus and an upwardly extending drainage duct for extracting the liquid portion of the foam upwardly from the rotatable member.

The same principle is also applicable to an apparatus 14b" according to the embodiment of FIG. 7, where the cylinder or sleeve 27'" surrounding the vanes 19 of the rotor 17'" is of the same length as the vanes. Here, however, the sleeve 27'" is provided at its upper end region, i.e., the end region where the gas exhaust opening is located, with a plurality of circumferentially distributed radial openings 32 and an exterior upwardly open collecting channel 33 of appropriate volume which is in communication with the interior of the sleeve through the openings 32. The intake end section 21a'" of the vertically upwardly extending drainage duct 21'" projects from above down into the channel 33 and has its inlet opening 30b positioned close to the bottom of the channel and oriented counter to the direction of rotation of the rotor 17'".

It will be understood that the foregoing description of preferred embodiments of the present invention is for purposes of illustration only, and that the various structural and operational features herein disclosed are susceptible to a number of modifications and changes none of which entails any departure from the spirit and scope of the present invention as defined in the hereto appended claims.

I claim:

1. In a method for controlling the foam in a vinegar fermentation process, in which the foam accumulating on the upper surface of the fermentation substrate within a fermentation tank is extracted from the latter and moved along a given path axially through a vaned rotor mounted for rotation about an axis substantially parallel to or coincident with the path, so that the foam, while moving along that path as the rotor is rotating, is subjected to centrifugal forces and is broken up thereby into a gas portion which is exhausted axially of the rotor in the direction of the path and a liquid portion, possibly still including some foam particles, which is separated from the gas portion in a direction radially of the rotor and the path;

the improvement comprising the step of conducting said separated liquid portion, along with any accompanying foam particles, away from the rotor without recirculating said separated liquid portion into the fermentation tank, so that said separated liquid portion is entirely eliminated from the fermentation process.

2. In the method of claim 1; the further improvement comprising the step of mixing said separated liquid portion, after the same has been eliminated from the fermentation process, with a quantity of vinegar end product which has been recovered from the fermentation process.

3. In the method of claim 2; the further improvement comprising the step of storing said separated liquid portion prior to the mixing thereof with said vinegar end product.

4. In the method of claims 1; the further improvement comprising the step of subjecting said separated liquid portion, after the same has been eliminated from the fermentation process, to a further processing independent of vinegar end product which has been recovered from the fermentation process.

5. In the method of claim 4; the further improvement comprising the step of storing said separated liquid portion prior to said further processing thereof.

6. In the method of claim 2; the further improvement comprising the step of subjecting said separated liquid portion, after the same has been eliminated from the fermentation process, but prior to the mixing thereof with said vinegar end product, to a further processing independent of said vinegar end product.

7. In the method of claim 6; the further improvement comprising the step of storing said separated liquid portion prior to said further processing thereof.

8. In an apparatus for controlling the foam generated in a fermentation tank in the course of a vinegar fermentation process, which apparatus includes a housing having opposite ends and defining between said ends a path of movement for foam extracted from said fermentation tank, said housing having at said opposite ends thereof a foam inlet and a gas exhaust, respectively, with said foam inlet being in communication with the interior of said fermentation tank in the region thereof where foam accumulates, said housing further having intermediate said opposite ends thereof a liquid discharge opening, a rotor disposed in said housing and mounted for rotation about an axis extending in the direction of said path of foam movement, said rotor having a plurality of substantially radial vanes spaced from one another circumferentially of the axis of rotation and defining between adjacent vanes a plurality of axial open-ended passageways, and drive means for rotating said rotor so that, upon rotation thereof, foam moving along said path through said passageways is subjected to centrifugal forces and is broken up into a gas portion which is exhausted axially of said rotor in the direction of said path and a liquid portion, possibly still including some foam particles, which is separated from the gas portion in a direction radially of said rotor and said path;

the improvement comprising a drainage duct communicating with said liquid discharge opening and terminating exteriorly of said fermentation tank for conducting said separated liquid portion away from said housing without permitting recirculation of said separated liquid portion to said fermentation substrate in said fermentation tank.

9. In an apparatus according to claim 8; the further improvement comprising a collecting vessel connected into said drainage duct, said collecting vessel being isolated from and out of communication with said fermentation tank.

10. In an apparatus according to claim 8 or 9; the further improvement comprising (a) that said rotor includes (i) a central hub to which said radial vanes are affixed and (ii) an exterior cylindrical sleeve connected to said radial vanes at the radially outer extremities thereof, (b) that said cylindrical sleeve is provided with a plurality of radial through openings providing egress for said separated liquid portion from said passageways into said housing, and (c) that a respective set of said openings is located adjacent each of said vanes in a respective region of said cylindrical sleeve which trails the immediately adjacent vane as viewed in the direction of rotation of said rotor.

11. In an apparatus according to claim 8; the further improvement comprising (a) that said rotor and said housing are mounted on said fermentation tank with said rotor being arranged for rotation about a horizontal axis, (b) that said foam inlet and said gas exhaust of said housing are constituted by respective vertical openings in said housing aligned with the ends of said rotor, (c) that a foam intake duct is connected between said fermentation tank and said foam inlet of said housing, and (d) that said drainage duct is disposed exteriorly of said fermentation tank.

12. In an apparatus according to claim 10; the further improvement comprising (e) that said rotor and said housing are mounted with at least said one end of said housing at which said foam inlet is defined being located within the interior of said fermentation tank, (f) that said liquid discharge opening is located adjacent said one end of said housing, and (g) that said drainage duct extends from said liquid discharge opening through said fermentation tank to the exterior of the latter.

13. In an apparatus for controlling the foam generated in a fermentation tank in the course of a vinegar fermentation process, which apparatus defines a path of movement for foam to be extracted from said fermentation tank and includes a rotor having opposite ends and mounted for rotation about an axis extending in the direction of said path of foam movement, said rotor having a plurality of substantially radial vanes spaced from one another circumferentially of said axis of rotation and defining between adjacent vanes a plurality of open-ended passageways, said rotor further providing at one end thereof a foam inlet to said passageways and at the other end a gas exhaust from said passageways, a liquid drainage duct communicating with said rotor, and drive means for rotating said rotor so that, upon rotation thereof, foam moving along said path through said passageways is subjected to centrifugal forces and is broken up into a gas portion which is exhausted axially of said rotor in the direction of said path and a liquid portion, possibly still including some foam particles, which is separated from the gas portion in a direction radially of said rotor and said path;

the improvement comprising (a) that said rotor includes (i) a central hub to which said radial vanes are affixed and (ii) an exterior cylindrical sleeve connected to said radial vanes at the radially outer extremities thereof, (b) that said cylindrical sleeve at said one end of said rotor has a section which extends beyond said radial vanes and against the interior surface of which said separated liquid portion is retained under the influence of centrifugal forces when said rotor is rotating, (c) that said liquid drainage duct has an intake opening (i) which is positioned closely adjacent said interior surface of said section of said cylindrical sleeve and (ii) which is oriented in a direction counter to the direction of rotation of said rotor, so that (iii) said separated liquid portion retained against said interior surface of said section of said cylindrical sleeve is forced into said liquid drainage duct as said rotor is rotating, and (d) that said liquid drainage duct terminates exteriorly of said fermentation tank for conducting said separated liquid portion away from said rotor without permitting recirculation of said separated liquid portion to said fermentation substrate in said fermentation tank.

14. In an apparatus according to claim 13; the further improvement comprising (e) that said rotor is mounted for rotation about a vertical axis, and (f) that said one end of said rotor is at the lower end of the latter so that said section of said cylindrical sleeve which extends beyond said radial vanes at that end of the rotor also constitutes said foam inlet to said rotor.

15. In an apparatus according to claim 14; the further improvement comprising (g) that a collecting channel is defined at said section of said cylindrical sleeve which extends beyond said radial vanes, and (h) that the section of said liquid drainage duct at which said intake opening of the latter is located projects into said collecting channel.

16. In an apparatus according to claim 13, 14 or 15; the further improvement comprising that a collecting vessel is connected into said liquid drainage duct, said collecting vessel being isolated from and out of communication with said fermentation tank.

17. In an apparatus for controlling the foam generated in a fermentation tank in the course of a vinegar fermentation process, which apparatus defines a path of movement for foam to be extracted from said fermentation tank and includes a rotor mounted for rotation about a vertical axis extending in the direction of said path of foam movement and having opposite upper and lower ends, said rotor further having a plurality of substantially radial vanes spaced from one another circumferentially of said axis of rotation and defining between adjacent vanes a plurality of open-ended passageways, with said lower end of said rotor constituting a foam inlet to said passageways and said upper end of said rotor constituting a gas exhaust from said passageways, a liquid drainage duct communicating with said rotor, and drive means for rotating said rotor so that, upon rotation thereof, foam moving along said path through said passageways is subjected to centrifugal forces and is broken up into a gas portion which is exhausted at said upper end and axially of said rotor in the direction of said path and a liquid portion, possibly still including some foam particles, which is separated from the gas portion in a direction radially of said rotor and said path;

the improvement comprising (a) that said rotor includes (i) a central hub to which said radial vanes are affixed and (ii) an exterior cylindrical sleeve connected to said radial vanes at the radially outer extremities thereof, (b) that a region of said cylindrical sleeve at said upper end of said rotor is provided with a plurality of openings through which said separated liquid portion can flow radially out of said rotor under the influence of centrifugal forces when said rotor is rotating, (c) that a collecting channel is provided exteriorly of said cylindrical sleeve in said region thereof at said upper end of said rotor, with the interior of said collecting channel being in communication with the interior of said cylindrical sleeve through said openings in the latter, (d) that said liquid drainage duct has an intake opening (i) which is positioned closely adjacent the interior surface of said collecting channel and (ii) which is oriented in a direction counter to the direction of rotation of said rotor, so that (iii) said separated liquid portion which enters and is retained in said collecting channel is forced into said liquid drainage duct as said rotor is rotating, and (e) that said liquid drainage duct terminates exteriorly of said fermentation tank for conducting said separated liquid portion away from said rotor without permitting recirculation of said separated liquid portion to said fermentation substrate in said fermentation tank.

18. In an apparatus according to claim 17; the further improvement comprising that a collecting vessel is connected into said liquid drainage duct, said collecting vessel being isolated from and out of communication with said fermentation tank.

* * * * *